United States Patent [19]

Nelson

[11] 4,111,995

[45] Sep. 5, 1978

[54] 2-DECARBOXY-2-HYDROXYMETHYL-ω-PHENOXY-PGD ANALOGS

[75] Inventor: Norman A. Nelson, Galesburgh, Mich.

[73] Assignee: The Upjohn Company, Kalamazoo, Mich.

[21] Appl. No.: 822,299

[22] Filed: Aug. 5, 1977

Related U.S. Application Data

[62] Division of Ser. No. 647,357, Jan. 8, 1976, Pat. No. 4,055,602.

[51] Int. Cl.$^2$ .............................................. C07C 49/84
[52] U.S. Cl. ................................................ 260/590 C
[58] Field of Search ..................... 260/590 C; 560/121

*Primary Examiner*—James O. Thomas, Jr.
*Assistant Examiner*—James H. Reamer
*Attorney, Agent, or Firm*—Robert A. Armitage

[57] ABSTRACT

This invention comprises certain analogs of the prostaglandins in which the C-1 carboxyl is replaced by a primary alcohol. Also provided in this invention, are novel chemical processes useful in the preparation of the above prostaglandin analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

83 Claims, No Drawings

2-DECARBOXY-2-HYDROXYMETHYL-ω-PHENOXY-PGD ANALOGS

The present application is a divisional application of Ser. No. 647,357, filed Jan. 8, 1976, now issued as U.S. Pat. No. 4,055,602.

The present invention relates to prostaglandin analogs, for which the essential material constituting disclosure therefor is incorporated by reference here from U.S. Pat. No. 4,055,602, issued Oct. 25, 1977.

I claim:

1. A prostaglandin analog of the formula

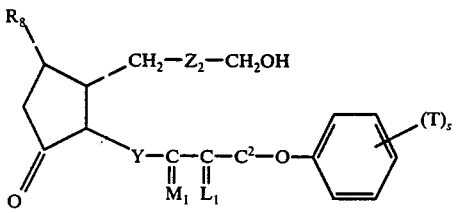

wherein $R_8$ is hydrogen or hydroxy;
wherein Y is trans-CH=CH—;
wherein $M_1$ is

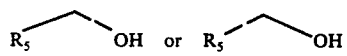

wherein $R_5$ is hydrogen or hydroxy;
wherein $L_1$ is

or a mixture of

wherein $R_3$ and $R_4$ are hydrogen or methyl, being the same or different;
wherein $Z_2$ is
cis-CH=CH—$CH_2$—$(CH_2)_g$—$CF_2$—;
cis-$CH_2$—CH=CH—$(CH_2)_g$—$CH_2$—; or
—$(CH_2)_3$—$(CH_2)_g$—$CF_2$—;
wherein $g$ is one, 2, or 3; and
wherein $s$ is zero, one, 2, or 3 and T is chloro, fluoro, trifluoromethyl, alkyl of one to 3 carbon atoms, inclusive, or alkoxy of one to 3 carbon atoms, inclusive, the various T's being the same or different, with the proviso that not more than two T's are other than alkyl.

2. A compound according to claim 1, wherein $R_8$ is hydrogen.

3. A compound according to claim 2, wherein $s$ is zero or one and T is chloro, fluoro, or trifluoromethyl.

4. A compound according to claim 3, wherein $Z_2$ is cis-CH=CH—$CH_2$—$(CH_2)_g$—$CF_2$—.

5. A compound according to claim 4, wherein $g$ is one.

6. A compound according to claim 5, wherein at least one of $R_3$ and $R_4$ is methyl.

7. A compound according to claim 6, wherein $R_3$ and $R_4$ are both methyl.

8. A compound according to claim 7, wherein $R_5$ is methyl.

9. 2-Decarboxy-2-hydroxymethyl-2,2-difluoro-15,16-dimethyl-16-phenoxy-18,19,20-trinor-9-deoxy-$PGD_2$, a compound according to claim 8.

10. A compound according to claim 7, wherein $R_5$ is hydrogen.

11. 2-Decarboxy-2-hydroxymethyl-2,2-difluoro-16-methyl-16-phenoxy-18,19,20-trinor-9-deoxy-$PGD_2$, a compound according to claim 10.

12. A compound according to claim 5, wherein $R_3$ and $R_4$ are both hydrogen.

13. A compound according to claim 12, wherein $R_5$ is methyl.

14. 2-Decarboxy-2-hydroxymethyl-2,2-difluoro-15-methyl-16-phenoxy-17,19,19,20-tetranor-9-deoxy-$PGD_2$, a compound according to claim 13.

15. A compound according to claim 12, wherein $R_5$ is hydrogen.

16. 2-Decarboxy-2-hydroxymethyl-2,2-difluoro-16-phenoxy-17,18,19,20-tetranor-9-deoxy-$PGD_2$, a compound according to claim 15.

17. A compound according to claim 3, wherein $Z_2$ is —$(CH_2)_3$—$(CH_2)_g$—$CF_2$—.

18. A compound according to claim 17, wherein $g$ is one.

19. A compound according to claim 18, wherein at least one of $R_3$ and $R_4$ is methyl.

20. A compound according to claim 19, wherein $R_3$ and $R_4$ are both methyl.

21. A compound according to claim 20, wherein $R_5$ is methyl.

22. 2-Decarboxy-2-hydroxymethyl-2,2-difluoro-15,16-dimethyl-16-phenoxy-18,19,20-trinor-9-deoxy-$PGD_1$, a compound according to claim 21.

23. A compound according to claim 20, wherein $R_5$ is hydrogen.

24. 2-Decarboxy-2-hydroxymethyl-2,2-difluoro-16-methyl-16-phenoxy-18,19,20-trinor-9-deoxy-$PGD_1$, a compound according to claim 23.

25. A compound according to claim 18, wherein $R_3$ and $R_4$ are both hydrogen.

26. A compound according to claim 25, wherein $R_5$ is methyl.

27. 2-Decarboxy-2-hydroxymethyl-2,2-difluoro-15-methyl-16-phenoxy-17,19,19,20-tetranor-9-deoxy-$PGD_1$, a compound according to claim 26.

28. A compound according to claim 25, wherein $R_5$ is hydrogen.

29. 2-Decarboxy-2-hydroxymethyl-2,2-difluoro-16-phenoxy-17,19,19,20-tetranor-9-deoxy-$PGD_1$, a compound according to claim 28.

30. A compound according to claim 3, wherein $Z_2$ is cis-$CH_2$—CH=CH—$(CH_2)_g$—$CH_2$—.

31. A compound according to claim 30, wherein $g$ is one.

32. A compound according to claim 31, wherein at least one of $R_3$ and $R_4$ is methyl.

33. A compound according to claim 32, wherein $R_3$ and $R_4$ are both methyl.

34. A compound according to claim 33, wherein $R_5$ is methyl.

35. 2-Decarboxy-2-hydroxymethyl-cis-4,5-didehydro-15,16-dimethyl-16-phenoxy-18,19,20-trinor-9-deoxy-$PGD_1$, a compound according to claim 34.

36. A compound according to claim 33, wherein $R_5$ is hydrogen.

37. 2-Decarboxy-2-hydroxymethyl-cis-4,5-didehydro-16-methyl-16-phenoxy-18,19,20-trinor-9-deoxy-PGD$_1$, a compound according to claim 36.

38. A compound according to claim 31, wherein R$_3$ and R$_4$ are both hydrogen.

39. A compound according to claim 38, wherein R$_5$ is methyl.

40. 2-Decarboxy-2-hydroxymethyl-cis-4,5-didehydro-15-methyl-16-phenoxy-17,18,19,20-tetranor-9-deoxy-PGD$_1$, a compound according to claim 39.

41. A compound according to claim 38, wherein R$_5$ is hydrogen.

42. 2-Decarboxy-2-hydroxymethyl-cis-4,5-didehydro-16-phenoxy-17,19,19,20-tetranor-9-deoxy-PGD$_1$, a compound according to claim 41.

43. A compound according to claim 1, wherein R$_8$ is hydroxy.

44. A compound according to claim 43, wherein s is zero or one and T is chloro, fluoro, or trifluoromethyl.

45. A compound according to claim 44, wherein Z$_2$ is cis-CH=CH—CH$_2$—(CH$_2$)$_g$—CF$_2$—.

46. A compound according to claim 45, wherein g is one.

47. A compound according to claim 46, wherein at least one of R$_3$ and R$_4$ is methyl.

48. A compound according to claim 47, wherein R$_3$ and R$_4$ are both methyl.

49. A compound according to claim 48, wherein R$_5$ is methyl.

50. 2-Decarboxy-2-hydroxymethyl-2,2-difluoro-15,16-dimethyl-16-phenoxy-18,19,20-trinor-PGD$_2$, a compound according to claim 49.

51. A compound according to claim 48, wherein R$_5$ is hydrogen.

52. 2-Decarboxy-2-hydroxymethyl-2,2-difluoro-16-methyl-16-phenoxy-18,19,20-trinor-PGD$_2$, a compound according to claim 51.

53. A compound according to claim 46, wherein R$_3$ and R$_4$ are both hydrogen.

54. A compound according to claim 53, wherein R$_5$ is methyl.

55. 2-Decarboxy-2-hydroxymethyl-2,2-difluoro-15-methyl-16-phenoxy-17,18,19,20-tetranor-PGD$_2$, a compound according to claim 54.

56. A compound according to claim 53, wherein R$_5$ is hydrogen.

57. 2-Decarboxy-2-hydroxymethyl-2,2-difluoro-16-phenoxy-17,18,19,20-tetranor-PGD$_2$, a compound according to claim 56.

58. A compound according to claim 44, wherein Z$_2$ is —(CH$_2$)$_3$—(CH$_2$)$_g$—CF$_2$—.

59. A compound according to claim 58, wherein g is one.

60. A compound according to claim 59, wherein at least one of R$_3$ and R$_4$ is methyl.

61. A compound according to claim 60, wherein R$_3$ and R$_4$ are both methyl.

62. A compound according to claim 61, wherein R$_5$ is methyl.

63. 2-Decarboxy-2-hydroxymethyl-2,2-difluoro-15,16-dimethyl-16-phenoxy-18,19,20-trinor-PGD$_1$, a compound according to claim 62.

64. A compound according to claim 61, wherein R$_5$ is hydrogen.

65. 2-Decarboxy-2-hydroxymethyl-2,2-difluoro-16-methyl-16-phenoxy-18,19,20-trinor-PGD$_1$, a compound according to claim 64.

66. A compound according to claim 60, wherein R$_3$ and R$_4$ are both hydrogen.

67. A compound according to claim 66, wherein R$_5$ is methyl.

68. 2-Decarboxy-2-hydroxymethyl-2,2-difluoro-15-methyl-16-phenoxy-17,18,19,20-tetranor-PGD$_1$, a compound according to claim 67.

69. A compound according to claim 66, wherein R$_5$ is hydrogen.

70. 2-Decarboxy-2-hydroxymethyl-2,2-difluoro-16-phenoxy-17,19,19,20-tetranor-PGD$_1$, a compound according to claim 69.

71. A compound according to claim 44, wherein Z$_2$ is cis-CH$_2$—CH=CH—(CH$_2$)$_g$—CH$_2$—.

72. A compound according to claim 71, wherein g is one.

73. A compound according to claim 72, wherein at least one of R$_3$ and R$_4$ is methyl.

74. A compound according to claim 73, wherein R$_3$ and R$_4$ are both methyl.

75. A compound according to claim 74, wherein R$_5$ is methyl.

76. 2-Decarboxy-2-hydroxymethyl-cis-4,5-didehydro-15,16-dimethyl-16-phenoxy-18,19,20-trinor-PGD$_1$, a compound according to claim 75.

77. A compound according to claim 74, wherein R$_5$ is hydrogen.

78. 2-Decarboxy-2-hydroxymethyl-cis-4,5-didehydro-16-methyl-16-phenoxy-18,19,20-trinor-PGD$_1$, a compound according to claim 77.

79. A compound according to claim 72, wherein R$_3$ and R$_4$ are both hydrogen.

80. A compound according to claim 79, wherein R$_5$ is methyl.

81. 2-Decarboxy-2-hydroxymethyl-cis-4,5-didehydro-15-methyl-16-phenoxy-17,18,19,20-tetranor-PGD$_1$, a compound according to claim 80.

82. A compound according to claim 79, wherein R$_5$ is hydrogen.

83. 2-Decarboxy-2-hydroxymethyl-cis-4,5-didehydro-16-phenoxy-17,18,19,20-tetranor-PGD$_1$, a compound according to claim 82.

* * * * *

UNITED STATES PATENT OFFICE
CERTIFICATE OF CORRECTION

Patent No. 4,111,995  Dated September 5, 1978

Inventor(s) Norman A. Nelson

It is certified that error appears in the above-identified patent and that said Letters Patent are hereby corrected as shown below:

Column 1, lines 15-22, that portion of the formula reading

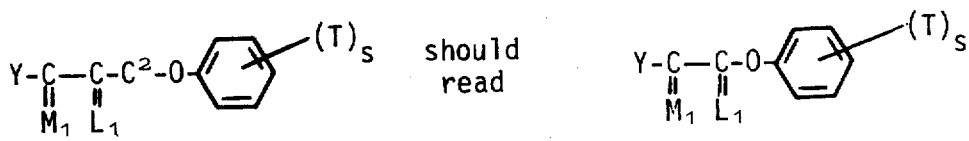

Column 1, line 32, "hydrogen or hydroxy;" should read -- hydrogen or methyl; --;

Column 2, lines 16, 47, and 52, "17,19,19,20" should read -- 17,18,19,20 --;

Column 3, line 14 and column 4, line 23, "17,19,19,20" should read -- 17, 18, 19, 20 --.

Signed and Sealed this

Twenty-second Day of May 1979

[SEAL]

Attest:

RUTH C. MASON
Attesting Officer

DONALD W. BANNER
Commissioner of Patents and Trademarks